United States Patent
Hou

(10) Patent No.: US 6,827,704 B1
(45) Date of Patent: Dec. 7, 2004

(54) SAFETY SYRINGE

(76) Inventor: Ching Chao Hou, 235 Chung-Ho Box 8-24, Taipei (TW)

( * ) Notice: Subject to any disclaimer, the term of this patent is extended or adjusted under 35 U.S.C. 154(b) by 0 days.

(21) Appl. No.: 10/437,607

(22) Filed: May 15, 2003

(51) Int. Cl.[7] .......................... A61M 5/00; A61M 5/315; A61M 5/32
(52) U.S. Cl. ........................ 604/110; 604/229; 604/195
(58) Field of Search ................................ 604/110, 218, 604/229, 240, 192, 195

(56) References Cited

U.S. PATENT DOCUMENTS

| | | | | |
|---|---|---|---|---|
| 5,308,329 A | * | 5/1994 | Mazur et al. ................ | 604/110 |
| 5,401,246 A | * | 3/1995 | Mazur et al. ................ | 604/110 |
| 5,578,015 A | * | 11/1996 | Robb .......................... | 604/195 |
| 6,458,105 B1 | * | 10/2002 | Rippstein et al. ............ | 604/195 |
| 6,761,707 B2 | * | 7/2004 | Huang et al. ................ | 604/240 |
| 2003/0212371 A1 | * | 11/2003 | Smith et al. ................ | 604/229 |

* cited by examiner

Primary Examiner—Sharon Kennedy

(57) ABSTRACT

A safety syringe is disclosed. A plurality of axial slits are formed in the outer wall of the unidirectional buckling chamber of the seat. An inner wall of the unidirectional buckling chamber has a second unidirectional buckling lip. A buckling head at a front end of the rod head of the push rod is installed with a unidirectional buckling lip; the third unidirectional buckling lip is installed with a plurality of slits so that the third unidirectional buckling lip is elastic. Thereby, by the axial slits of the unidirectional buckling chamber and the slits of the third unidirectional buckling lip, when the push rod is pushed to a foremost end, the buckling head at the front end of the rod head is pushed into the unidirectional buckling chamber at the rear end of the rod head of the push rod.

1 Claim, 10 Drawing Sheets

SAFETY SYRINGE

FIELD OF THE INVENTION

The present invention relates to syringes, and particularly to a safety syringe having a simple structure so that it can not be reused.

BACKGROUND OF THE INVENTION

With reference to FIGS. 1 to 4, the prior art syringe includes a syringe 10, a seat 20 and a push rod 30.

The syringe 10 is a round cylinder penetrated from the front end to the rear end. A stop wall 11 is radially arranged to be at an inner wall of the syringe 10 near the front end thereof. An annular first unidirectional buckling lip 13 is installed at an inner wall of the rear side of the syringe 10.

A front end of the seat 20 is a sleeve 21 for connecting a needle 40. A seat has a liquid flow channel 22 which penetrates the front and rear ends of the syringe and at an axial center thereof. A rear end of the liquid flow channel 22 is formed with an unidirectional buckling chamber 23. An outer wall of the seat 20 is formed with an annular groove 24 with respect to the first lip 12 at a front end of the syringe 10.

The front end of the push rod 30 has a rod head 31. A plurality of connecting points 32 serves for connecting the push rod 30 with he rod head 31 so as to be formed as a breaking section 33 by which the rod head 31 is broken after use. The rod head 31 has a second water-stop ring 34. A front end of the rod head 31 has a tapered buckling head 35.

By above mentioned structure, the seat 20 and rod head 31 of the push rod 30 can enter into the syringe 10. Then, the seat 20 can be pushed into the first lip 12 at the front end of the syringe 10 so as to be buckled to a front end of the syringe 10. The sleeve 21 at a front end of the seat 20 protrudes from the front end of the syringe 10. Thereby, needle 40 can be screwed into the syringe 10 (referring to FIG. 1). When the push rod 30 is pushed to a foremost end, the buckling head 35 at the front end of the rod head 31 can be pressed into the unidirectional buckling chamber 23 at a rear end of the seat 20 (referring to FIG. 2). Next, the push rod 30 is pulled backwards and at the same time, the seat 20 is retracted so that the needle 40 can be placed into the syringe 10 (referring to FIG. 3). Further, the needle 40 is retracted to be stored in the syringe 10. Then the rod head 31 is broken to separate from the push rod 30 (referring to FIG. 4). Thereby, the syringe 10 can be not reused. Thereby, the object of safety is achieved.

However when the push rod 30 is pushed to the foremost end (referring to FIG. 5), the buckling head 35 at the foremost is plugged into the unidirectional buckling chamber 23 at the rear end of the seat 20 so that the seat 30 is firmly secured to the push rod 30. When the push rod 30 is pulled backwards, the seat 30 can be pulled out at the same time. Thereby, the needle 40 is stored in the syringe 10. Thus, the buckling head 35 at the front end of the push rod 30 is easily plugged into the unidirectional buckling chamber 23 at the rear end of the seat 20. To cause that the buckling head 35 will not separate from the unidirectional buckling chamber 23 and can drive the seat 20 to move backwards when the push rod 30 moves backwards. A high precision is necessary so that it is difficult to make, maintain and prepare a mold. As a result, the cost is increased Moreover, to control the precision of the buckling head 35 and the unidirectional buckling chamber 23 is difficult so that the quality can not be well controlled.

Further, a front end of the liquid flow channel 22 of the seat 20 has a space which would accumulates drugs therein so that when the push rod 30 is pushed to the foremost end, part of the drug will flow into the liquid flow channel 22. The amount of the drug is over the international standard, 0.075 ml.

SUMMARY OF THE INVENTION

Accordingly, the primary object of the present invention is to provide a safety syringe, which can improve prior art defects as mentioned above.

To achieve above objects, the present invention provides a safety syringe, wherein plurality of axial slits are formed in the outer wall of the unidirectional buckling chamber of the seat. An inner wall of the unidirectional buckling chamber has a second unidirectional buckling lip. A buckling head at a front end of the rod head of the push rod is installed with a unidirectional buckling lip; the third unidirectional buckling lip is installed with a plurality of slits so that the third unidirectional buckling lip is elastic. Thereby, by the axial slits of the unidirectional buckling chamber and the slits of the third unidirectional buckling lip, when the push rod is pushed to a foremost end, the buckling head at the front end of the rod head is pushed into the unidirectional buckling chamber at the rear end of the rod head of the push rod. The buckling head at the front end of the rod head of the push rod is extended with an axial strip. When the push rod is pushed to a foremost end, the axial strip is inserted into the liquid flow channel of the seat, the liquid in the liquid flow channel is pushed out so as to reduce the residue of the liquid so as to match the international standard.

The various objects and advantages of the present invention will be more readily understood from the following detailed description when read in conjunction with the appended drawing.

DETAILED DESCRIPTION OF THE PREFERRED EMBODIMENTS

Referring to FIGS. 6 to 12, the present invention will be described herein with the appended drawings.

Figure 1:
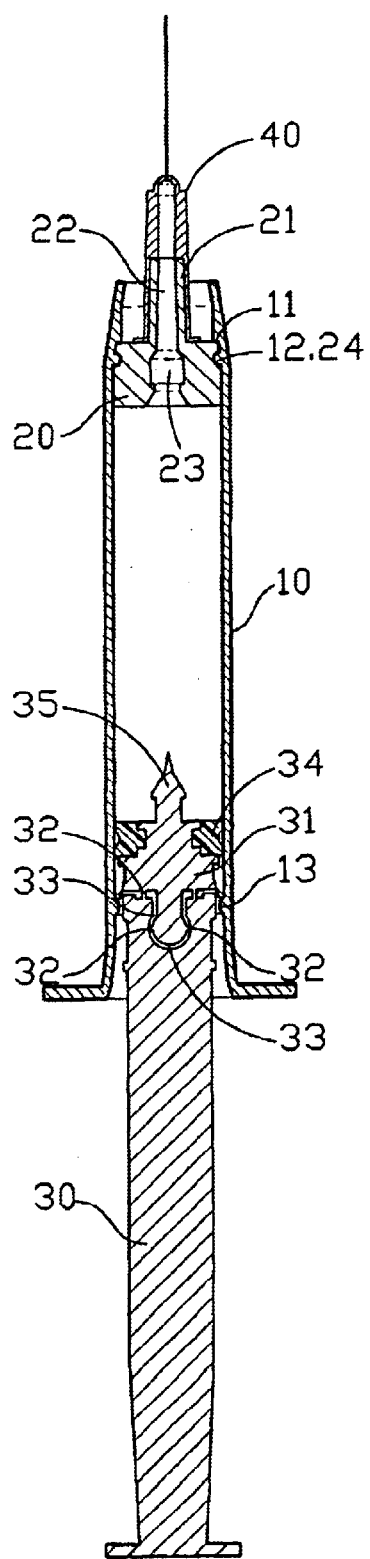
FIG. 1 is a cross section view showing the structure of a prior art syringe.
Figure 2:
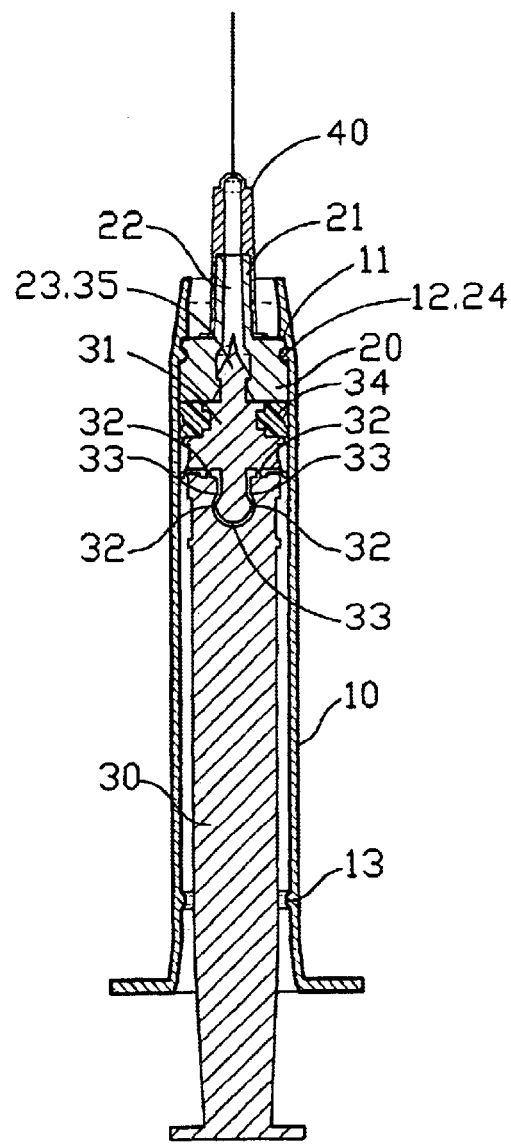
FIG. 2 is another cross section view showing the structure of a prior art syringe.
Figure 3:
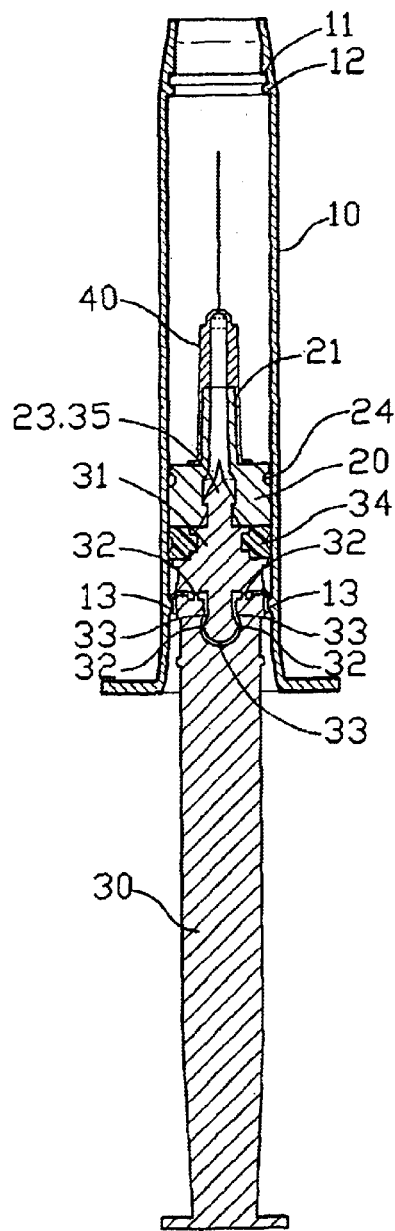
FIG. 3 is yet a cross section view showing the structure of a prior art syringe.
Figure 4:
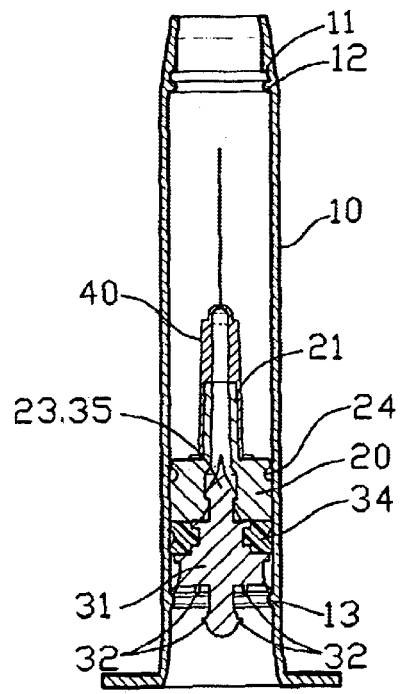
FIG. 4 is still a cross section view showing the structure of a prior art syringe.
Figure 4:
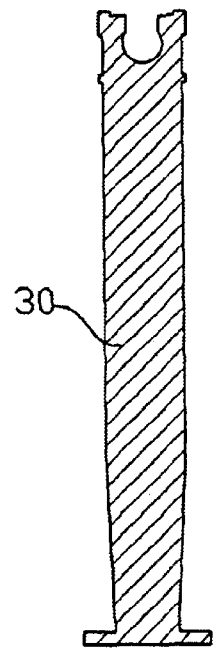
Figure 5:
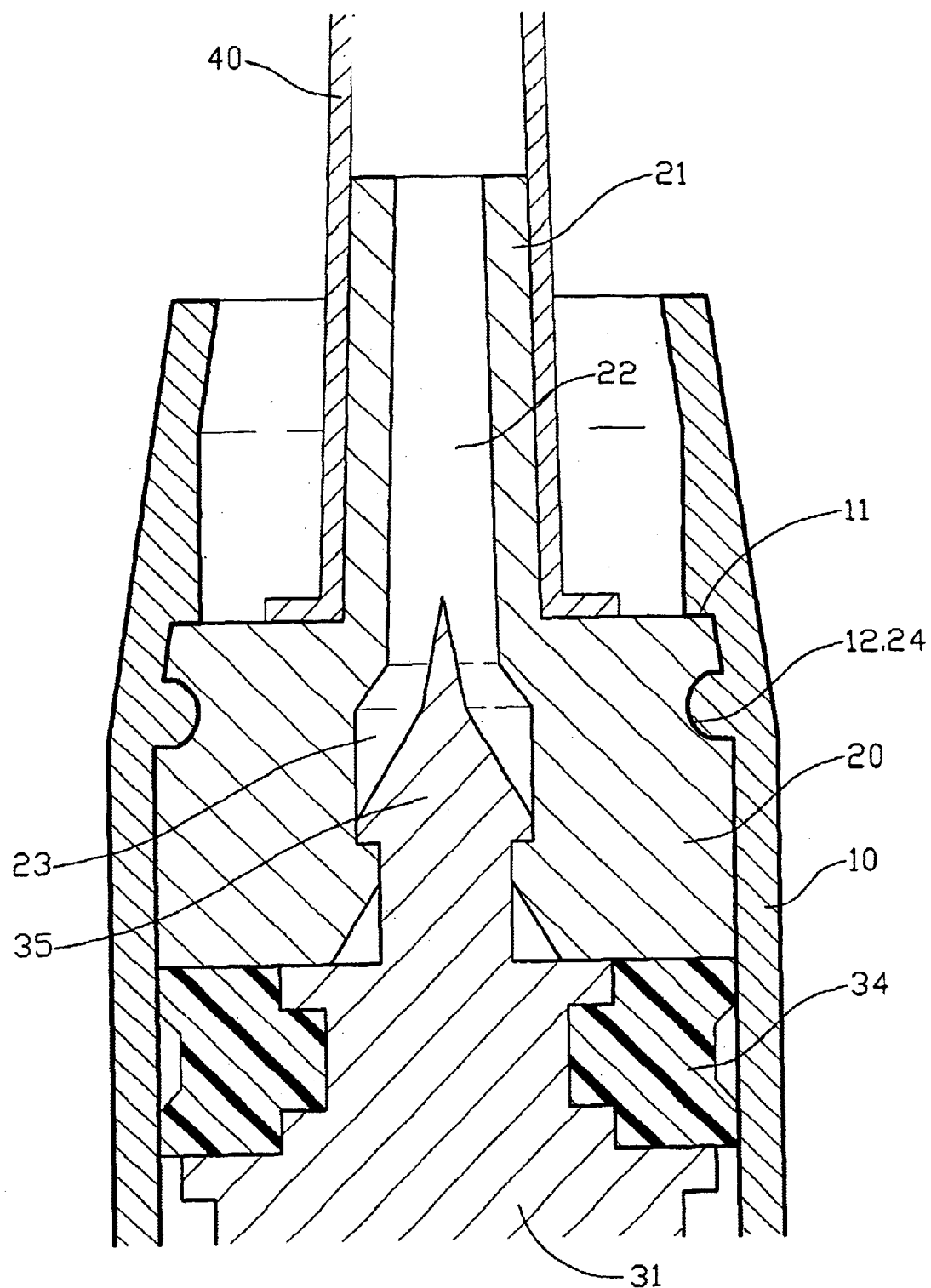
FIG. 5 is a partial cross section view showing that a prior art syringe seat is plugged into a front end of the syringe.
Figure 6:
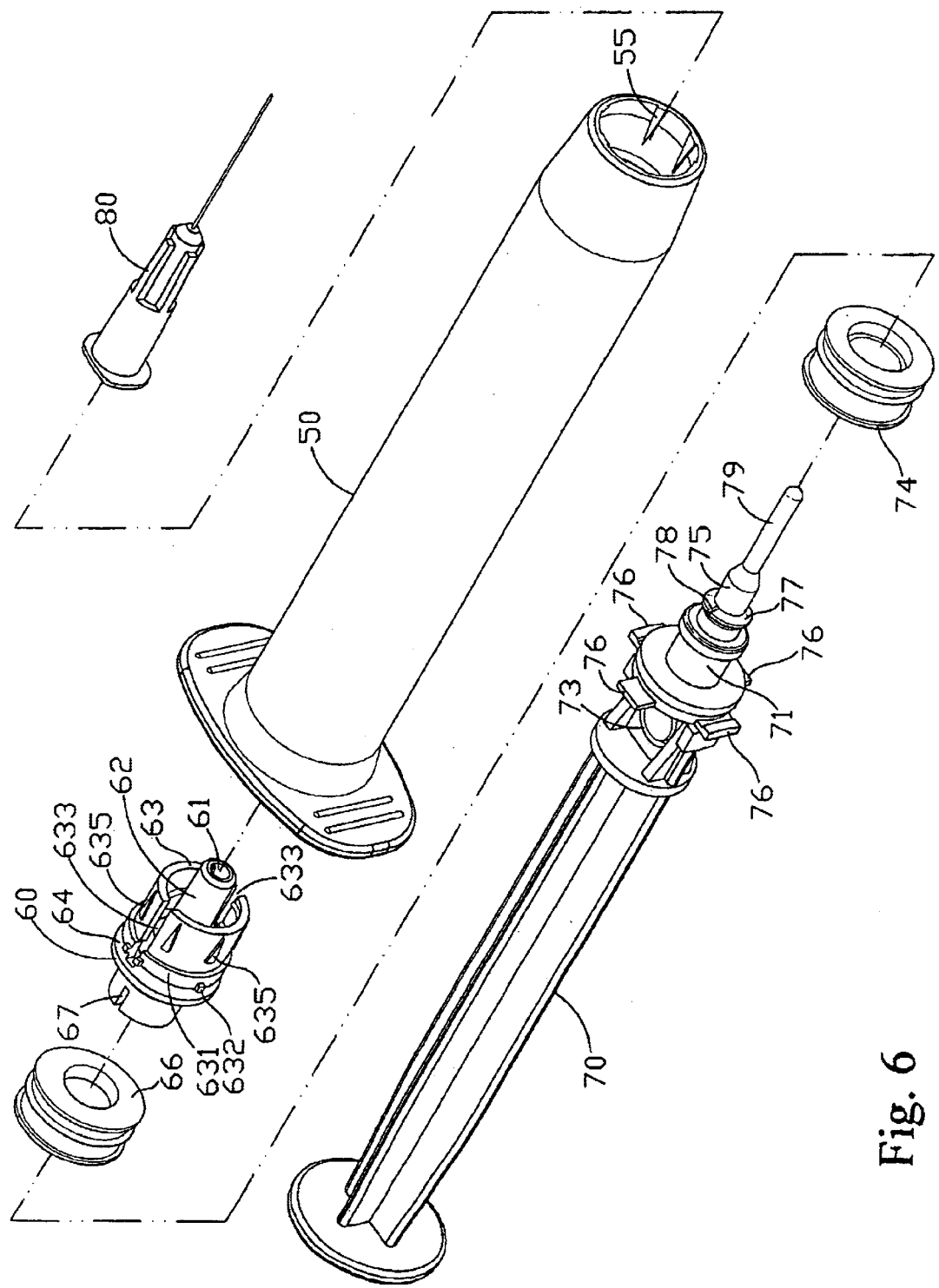
FIG. 6 shows the perspective view of the present invention.

With reference to FIG. 6, the present invention includes a syringe 50, a seat 60 and a push rod 70.

Figure 7:
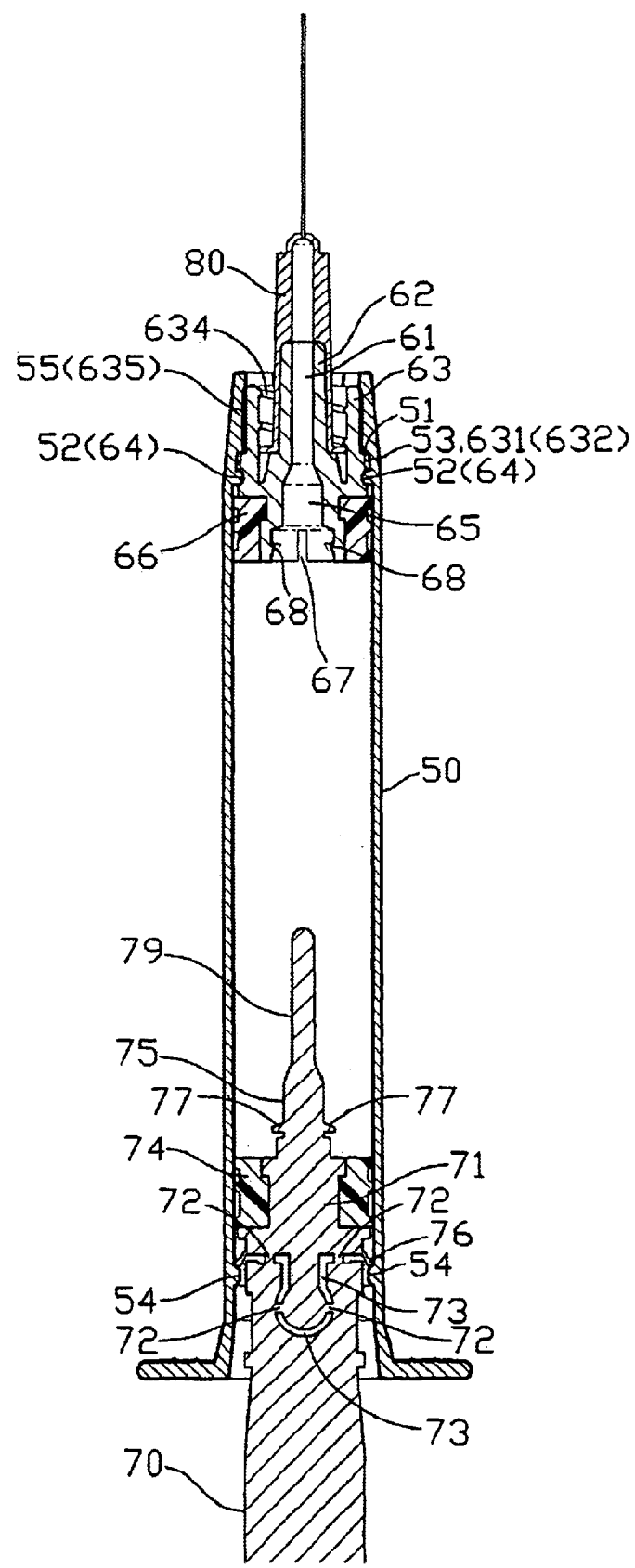
FIG. 7 is a first schematic cross section view of the present invention.
Figure 8:
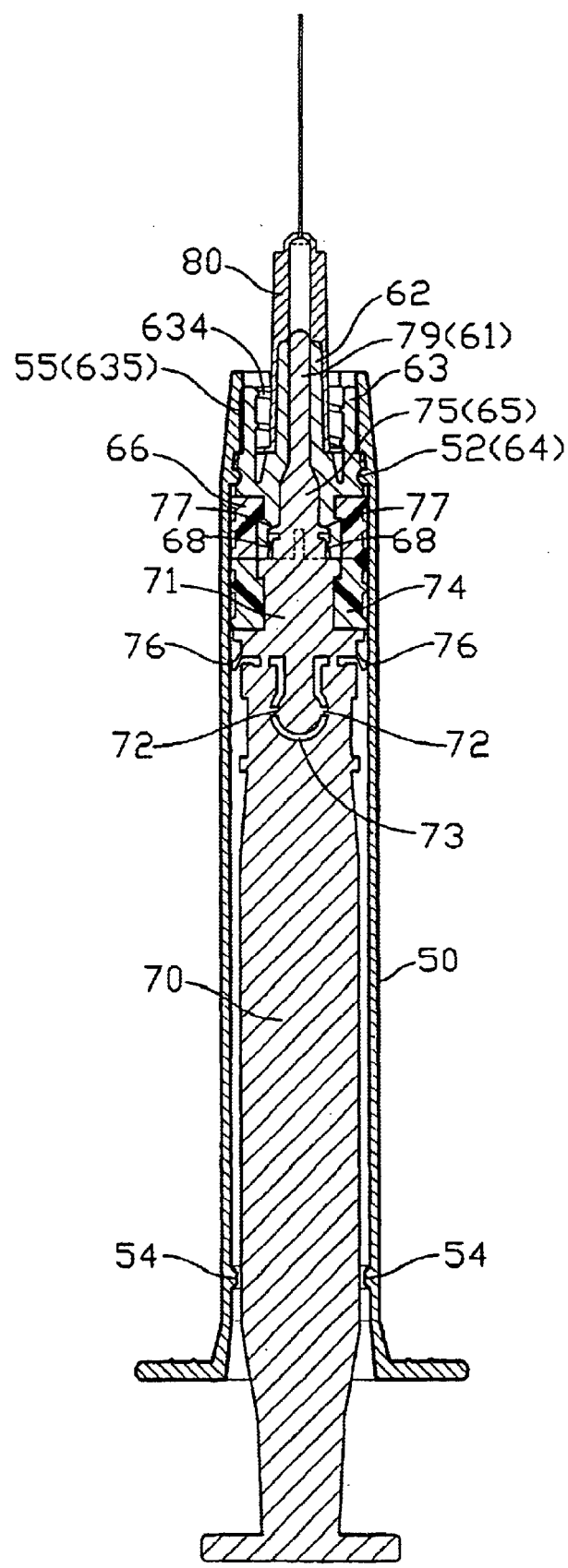
FIG. 8 is a second schematic cross section view of the present invention.
Figure 9:
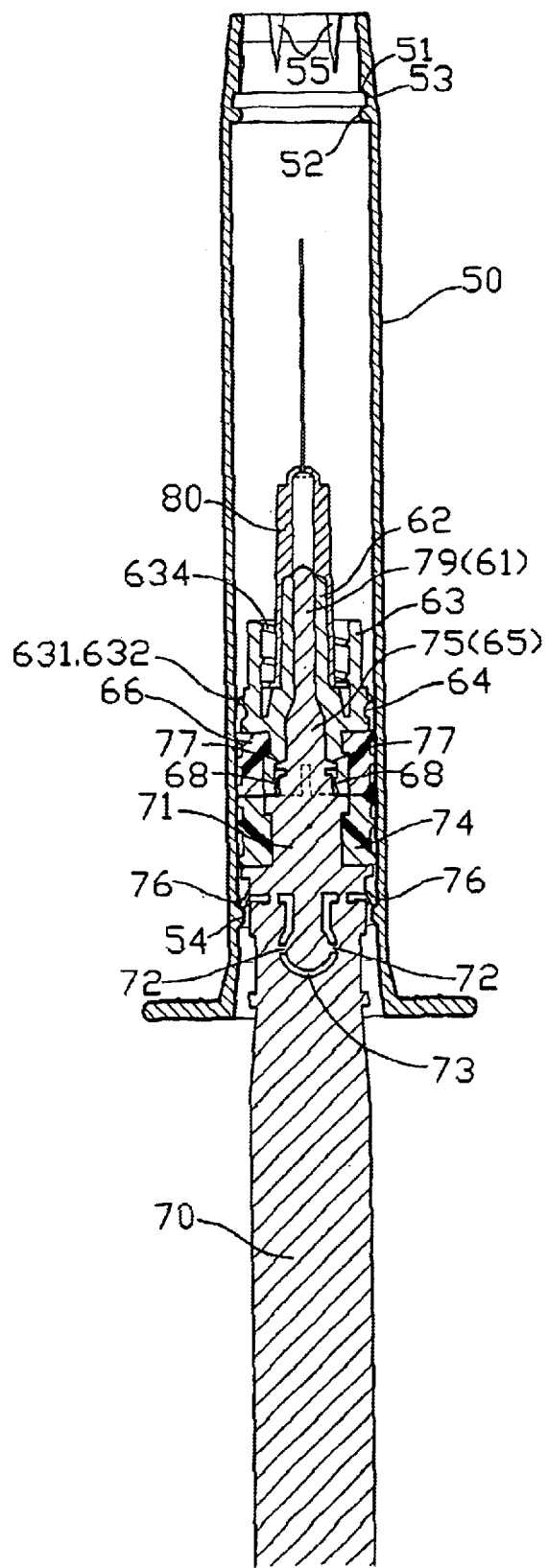
FIG. 9 is a third schematic cross section view of the present invention.
Figure 10:
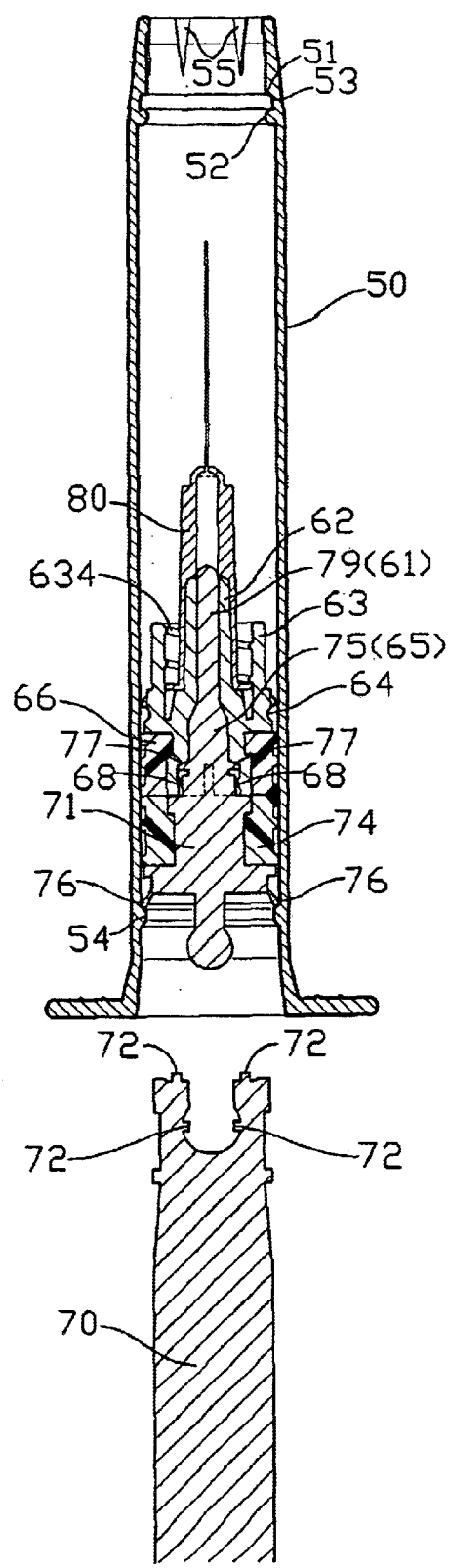
FIG. 10 is a fourth schematic cross section view of the present invention.
Figure 11:
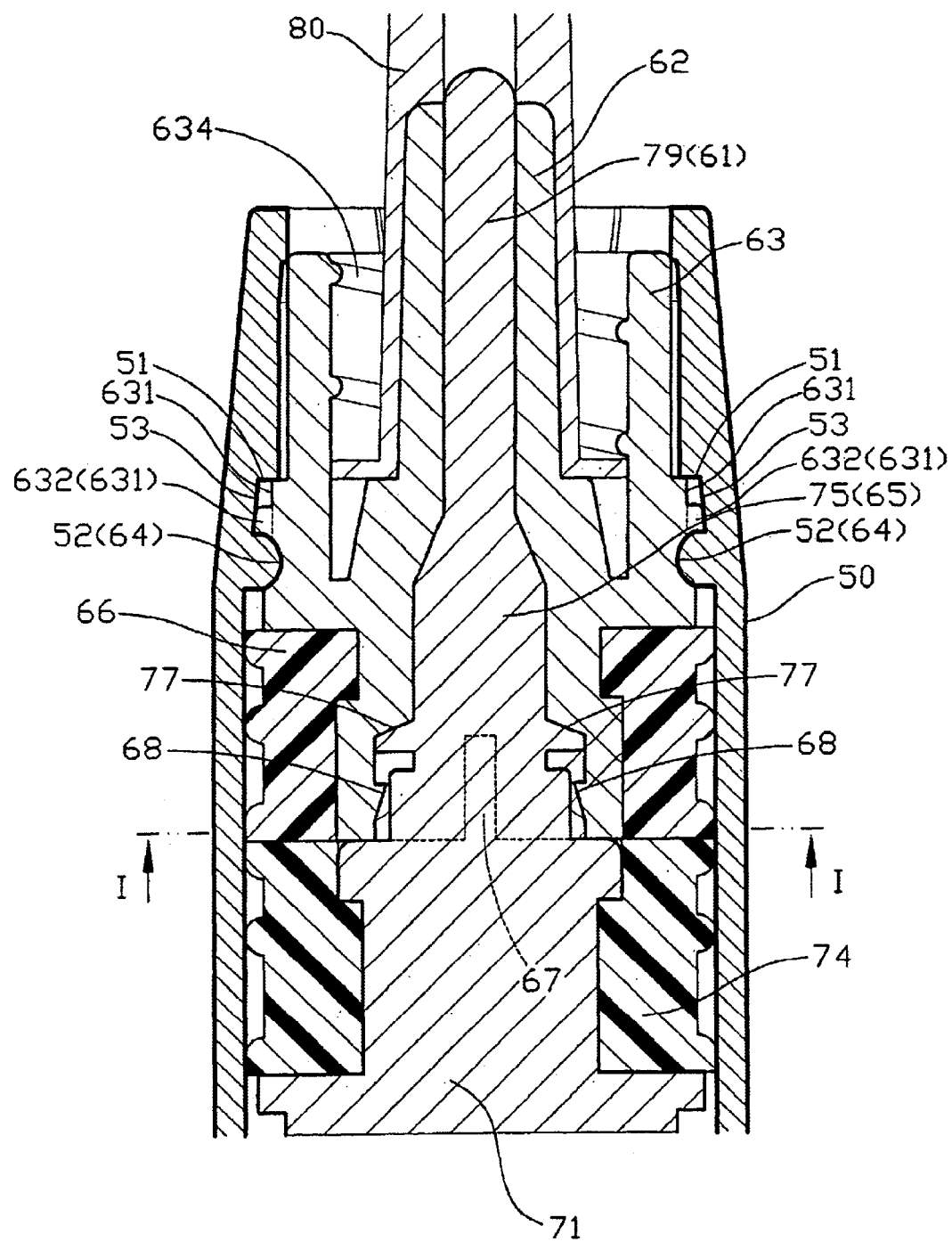
FIG. 11 is a partial enlarge cross section view showing that the seat of the present invention is plugged into a front end of a syringe.
Figure 12:
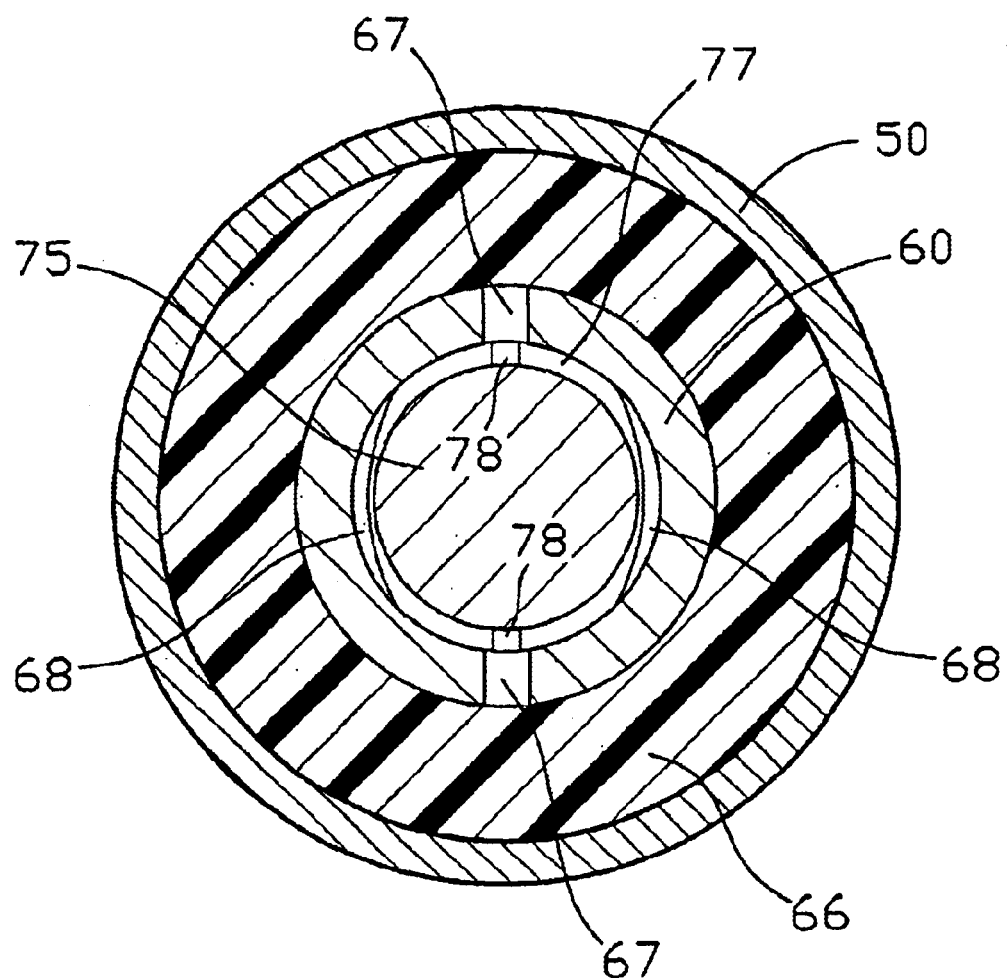
FIG. 12 is a cross section view along line I—I of FIG. 11.

The syringe 50, as shown in FIGS. 6 and 7, is a round cylinder penetrated from the front end to the rear end. A stop wall 52 is radially arranged to be at an inner wall of the syringe 50 near the front end thereof. An annular first lip is formed at a rear end of the stop wall. An annular groove 53 is formed between the rear side of the stop wall 51 and the first lip 52. An annular first unidirectional buckling lip 54 is installed at an inner wall of the rear side of the syringe 50.

Referring to FIGS. 6 and 7, a seat 60 has a liquid flow channel 61 which penetrates the front and rear ends of the syringe 50 and at an axial center thereof. A front end of the liquid flow channel 61 has a connecting end 62 for connecting a needle of the syringe 50. A periphery of the connecting end 62 has an enclosing wall 631. An outer wall of the enclosing wall 63 has a second lip 631 annularly arranged around the enclosing wall 63. The second lip 631 is exactly corresponding to the groove 53 at the front end syringe 50. A plurality of tips 632 are formed on the second lip 631 so as to increase the tightness of the seat 60 to the front end of the syringe 50. Moreover, in manufacturing, the preciseness of the seat 60 in manufacturing can be retained without being affected by the heat expansion and cool contraction. Thereby, the yield of the syringe can be increased and the syringe seat 60 can suffer from a larger pull force over 3 kg. An outer wall of the seat 60 has an annular slot 64 which is corresponding to the annular first lip 52 at the inner wall of the front end of the syringe 50. Moreover, the enclosing wall 63 has a plurality of axial slits 633 so that the enclosing wall 63 is reduceable. An inner wall of the enclosing wall 63 has an inner thread 634 for screwing the syringe needle 80 to the connecting end 62. A rear end of the liquid flow channel 61 has a unidirectional buckling chamber 65 and a first water-stop ring 66 is at a periphery of the unidirectional buckling chamber 65 for preventing drainage of liquid from the contact surface of the seat 60 and the syringe 50.

A push rod 70 (referring to FIGS. 6, 7) has a front end. The front end has a rod head 71. A plurality of connecting points 72 serve for connecting the push rod 70 with he rod head 71 so as to be formed as a breaking section 73 by which the rod head 71 is broken after use. The rod head 71 has a second water-stop ring 74. A front end of the rod head 71 has a tapered buckling head 75. An upper periphery of the rod head 71 is installed with a plurality of unidirectional buckling pieces 76.

By above mentioned structure, the seat 60 and rod head 71 of the push rod 70 can enter into the syringe 50. Then, the second lip 631 of the seat 60 can be pushed into the first lip 52 at the front end of the syringe 50 so as to be buckled to the groove 53 between the stop wall 51 and the first lip 52 so that the seat 60 is placed at a front end of the syringe 50. The sleeve 61 at a front end of the seat 60 protrudes from the front end of the syringe 50. Thereby, needle 80 can be screwed into the syringe 50 (referring to FIG. 7). When the push rod 70 is pushed to a foremost end, the buckling head 75 at the front end of the rod head 71 can be pressed into the unidirectional buckling chamber 65 at a rear end of the seat 60 (referring to FIG. 8). Next, the push rod 70 is pulled backwards and at the same time, the seat 60 is retracted so that the needle 80 can be placed into the syringe 50 (referring to FIG. 9). Further, the needle 80 is retracted to be stored in the syringe 50. Then the rod head 71 is broken to separate from the push rod 70 (referring to FIG. 10). Thereby, the syringe 50 can be not reused. Thereby, the object of safety is achieved.

However the structure is similar to the prior art. The features of the present invention will be described herein.

A plurality of axial slits 67 are formed in the outer wall of the unidirectional buckling chamber 65 of the seat 60. The inner wall of the unidirectional buckling chamber 65 has a second unidirectional buckling lip 68 (referring to FIG. 7). The buckling head 75 at a front end of the rod head 71 of the push rod 70 is installed with a third unidirectional buckling lip 77. The third unidirectional buckling lip 77 is installed with a plurality of slits 78 so that the third unidirectional buckling lip 17 is elastic. Thereby, by the axial slits 67 of the unidirectional buckling chamber 65 and the slits 78 of the third unidirectional buckling lip 17, when the push rod 70 is pushed to a foremost end (referring to FIGS. 8, 11 and 12), the buckling head 75 at the front end of the rod head 71 can be, pushed into the unidirectional buckling chamber 65 at the rear end of the rod head 71 of the push rod 70.

Further, the buckling head 75 at the front end of the rod head 71 of the push rod 70 is extended with an axial strip 79 (referring to FIG. 6). When the push rod 70 is pushed to a foremost end, the axial strip 77 can be inserted into the liquid flow channel 61 of the seat 60 (referring to FIG. 8), the liquid in the liquid flow channel 61 can be pushed out so as to reduce the residue of the liquid to match the international standard.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A safety syringe comprising:

a syringe being a round cylinder, the round cylinder penetrated from a front end thereof to a rear end thereof; a stop wall being radially arranged to be at an inner wall of the syringe near the front end thereof; an annular first lip being formed at a rear end of the stop wall; an annular groove being formed between a rear side of the stop wall and the first lip; an annular first unidirectional buckling lip being installed at an inner wall of the rear side of the syringe;

a seat having a liquid flow channel which penetrates the front and rear ends of the syringe and at an axial center thereof; a front end of the liquid flow channel having a connecting end for connecting with a needle of the syringe; a periphery of the connecting end having an enclosing wall; an outer wall of the enclosing wall having a second lip annularly arranged around the enclosing wall; the second lip being corresponding to the groove at the front end syringe; an outer wall of the seat having an annular slot which is corresponding to the annular first lip at the inner wall of the front end of the syringe; a rear end of the liquid flow channel having a unidirectional buckling chamber and a first water-stop ring being at a periphery of the unidirectional buckling chamber for preventing drainage of liquid from the contact surface of the seat and the syringe;

a push rod having a front end; the front end having a rod head; a plurality of connecting points serving for connecting the push rod with the rod head so as to be formed as a breaking section for breaking the rod head after use; the rod head having a second water-stop ring; a front end of the rod head having a tapered buckling head; an upper periphery of the rod head being installed with a plurality of unidirectional buckling pieces; characterized in that:

a plurality of axial slits are formed in the outer wall of the unidirectional buckling chamber of the seat; an inner wall of the unidirectional buckling chamber has a second unidirectional buckling lip; the buckling head at a front end of the rod head of the push rod is installed with a third unidirectional buckling lip; the third unidirectional buckling lip is installed with a plurality of slits so that the third unidirectional buckling lip is elastic; thereby, by the axial slits of the unidirectional buckling chamber and the slits of the third unidirectional buckling lip, when the push rod is pushed to a foremost end, the buckling head at the front end of the rod head is pushed into the unidirectional buckling chamber at the rear end of the rod head of the push rod; and the buckling head at the front end of the rod head of the push rod is extended with an axial strip; when the push rod is pushed to a foremost end, the axial strip is inserted into the liquid flow channel of the seat, the liquid in the liquid flow channel is pushed out so as to reduce the residue of the liquid.

* * * * *